United States Patent
Khair

(10) Patent No.: US 10,272,187 B2
(45) Date of Patent: Apr. 30, 2019

(54) SYSTEM AND METHODS FOR DIALYZER FLOW RATES ESTIMATION USING MEASURED DIALYZER PRESSURES

(71) Applicant: Fresenius Medical Care Holdings, Inc., Waltham, MA (US)

(72) Inventor: Mohammad M. Khair, Irvine, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 121 days.

(21) Appl. No.: 15/439,520

(22) Filed: Feb. 22, 2017

(65) Prior Publication Data

US 2018/0236152 A1 Aug. 23, 2018

(51) Int. Cl.
*A61M 1/16* (2006.01)
*B01D 61/22* (2006.01)
(Continued)

(52) U.S. Cl.
CPC ........ *A61M 1/1615* (2014.02); *A61M 1/1605* (2014.02); *A61M 1/1647* (2014.02);
(Continued)

(58) Field of Classification Search
None
See application file for complete search history.

(56) References Cited

U.S. PATENT DOCUMENTS

| 4,731,731 A | 3/1988 | Cochran |
| 7,938,792 B2 | 5/2011 | Roger et al. |

(Continued)

FOREIGN PATENT DOCUMENTS

| EP | 0204174 A2 * | 12/1986 | ............. A61M 1/16 |
| WO | WO 95/022743 A1 | 8/1995 | |

(Continued)

OTHER PUBLICATIONS

Braun NPL—Dialog+ Dialysis Machine, B. Braun Avitum AG, Rev. 2.02, May 2010 (Year: 2010).*

(Continued)

*Primary Examiner* — Krishnan S Menon
*Assistant Examiner* — Bradley R Spies
(74) *Attorney, Agent, or Firm* — Leydig, Voit & Mayer, Ltd.

(57) ABSTRACT

Embodiments of the disclosure include a method and system for estimating flow rates of a fluid or medium though a dialyzer during a dialysis treatment (e.g., a hemodialysis treatment). Pressure sensors are incorporated in dialyzers used for hemodialysis to achieve continuous monitoring of fluid balance of the body. During dialysis, obtaining fluid input and output pressures experienced at various inlets and outlets of dialyzers is easier than obtaining flow rates at these inlets and outlets, but using flow rates is better in determining the effectiveness of a dialyzer during hemodialysis. Embodiments of the disclosure thus use pressure measurements at inlets and outlets of a dialyzer along with a dialyzer model to determine fluid flow rates through the dialyzer. The fluid flow rates are used to determine whether there are leakages or occlusions in tubing during the dialysis treatment.

20 Claims, 12 Drawing Sheets

(51) Int. Cl.
  *B01D 61/32* (2006.01)
  *A61M 1/36* (2006.01)

(52) U.S. Cl.
  CPC .......... *A61M 1/3639* (2013.01); *B01D 61/22* (2013.01); *B01D 61/32* (2013.01); *A61M 2205/15* (2013.01); *A61M 2205/18* (2013.01); *A61M 2205/3306* (2013.01); *A61M 2205/3331* (2013.01); *A61M 2205/3334* (2013.01); *A61M 2205/70* (2013.01)

(56) References Cited

U.S. PATENT DOCUMENTS

| | | |
|---|---|---|
| 8,137,553 B2 | 3/2012 | Fulkerson et al. |
| 8,529,491 B2 | 9/2013 | Beiriger |
| 8,597,505 B2 | 12/2013 | Fulkerson et al. |
| 2008/0108930 A1 | 5/2008 | Weitzel et al. |
| 2009/0024070 A1 | 1/2009 | Gelfand et al. |
| 2009/0043240 A1 | 2/2009 | Robinson et al. |
| 2011/0315611 A1 | 12/2011 | Fulkerson et al. |
| 2013/0204174 A1 | 8/2013 | Olde et al. |
| 2013/0204542 A1 | 8/2013 | Olde et al. |
| 2014/0119954 A1 | 5/2014 | Schweitzer et al. |
| 2014/0205981 A1* | 7/2014 | Ryder .................. G09B 19/00 434/262 |

FOREIGN PATENT DOCUMENTS

| | | |
|---|---|---|
| WO | WO 2012/095827 A1 | 7/2012 |
| WO | WO 2016/057982 A1 | 4/2016 |

OTHER PUBLICATIONS

Guo et al, "Sensor Failure Detection and Recovery by Neural Networks," NASA Technical Memorandum 104484 (Jul. 8, 1991).
International Patent Application No. PCT/US2018/018003, Search Report (dated Apr. 9, 2018).

* cited by examiner

SYSTEM AND METHODS FOR DIALYZER FLOW RATES ESTIMATION USING MEASURED DIALYZER PRESSURES

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a dialyzer which removes unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. The fresh dialysate collects excess impurities passing through the straw-like tubes by diffusion, and also collects excess water through an ultrafiltration process due to a pressure drop across the membranes. The used dialysate exits the dialyzer with the excess fluids and toxins via an output tube, thus cleansing the blood flowing through the dialyzer. The dialyzed blood then flows out of the dialyzer via tubing and a needle (or catheter) back into the patient. Sometimes, a heparin drip or pump is provided along the extracorporeal blood flow loop in order to prevent clotting during the hemodialysis process. Several liters of excess fluid can be removed during a typical multi-hour treatment session. In the U.S., a chronic patient will normally undergo hemodialysis treatment in a dialysis center three times per week, either on a Monday-Wednesday-Friday schedule or a Tuesday-Thursday-Saturday schedule.

SUMMARY

One exemplary embodiment of the disclosure provides a system for monitoring ultrafiltration rate during hemodialysis using estimated flow rates. The system includes a dialyzer, at least one pressure sensor coupled to the dialyzer, a non-transitory computer readable medium with one or more models stored thereon, and a processor. The processor is configured to: acquire pressure readings from the at least one pressure sensor, apply the pressure readings to the one or more models to determine an estimated flow rate, determine whether the estimated flow rate and the expected flow rate are within a predefined range, and make adjustments and/or generate an alarm in response to determining that the estimated flow rate and the expected flow rate are not within the predefined range.

Another exemplary embodiment of the disclosure provides a method for monitoring ultrafiltration rate during hemodialysis using estimated flow rates. The method is performed by an electronic device with a processor and a non-transitory computer readable medium with one or more models stored thereon. The method includes acquiring pressure readings from at least one pressure sensor in a dialyzer, applying the pressure readings to the one or more models to determine an estimated flow rate, determining whether the estimated flow rate and the expected flow rate are within a predefined range, and making adjustments and/or generating an alarm in response to determining that the estimated flow rate and the expected flow rate are not within the predefined range.

Yet another exemplary embodiment of the disclosure provides a non-transitory computer readable medium for monitoring ultrafiltration rate during hemodialysis using estimated flow rates. The non-transitory computer readable medium contains processor-executable instructions that facilitate performance of a method by a computer when executed. The method includes: acquiring pressure readings from at least one pressure sensor in a dialyzer, wherein the dialyzer comprises four ports, a first port connected to an arterial blood line, a second port connected to a venous blood line, a third port connected to a dialysate in line, and a fourth port connected to a dialysate out line, and wherein the at least one pressure sensor comprises four pressure sensors, a first pressure sensor measuring pressure at an arterial blood line, a second pressure sensor measuring pressure at a venous blood line, a third pressure sensor measuring pressure at a dialysate in line, and a fourth pressure sensor measuring pressure at a dialysate out line; applying the pressure readings to the one or more models to determine an estimated flow rate; determining whether the estimated flow rate and the expected flow rate are within a predefined range; and making adjustments and/or generating an alarm in response to determining that the estimated flow rate and the expected flow rate are not within the predefined range.

DETAILED DESCRIPTION

Figure 1:
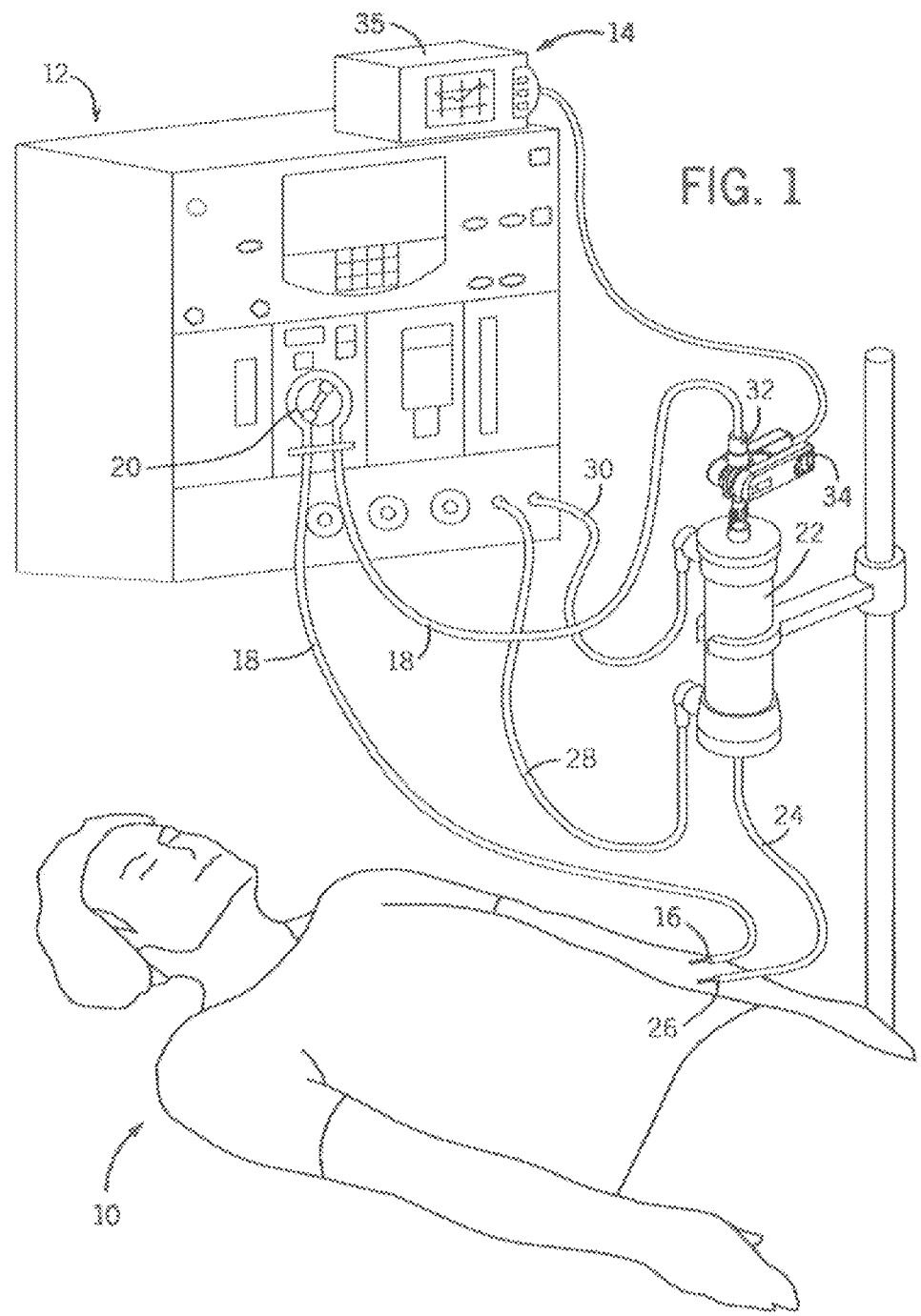
FIG. 1 is a perspective view of a typical patient undergoing hemodialysis treatment with a non-invasive, optical blood monitor monitoring the patient's blood in real-time as it passes through extracorporeal tubing in the hemodialysis system.

Hemodialysis has an acute impact on the fluid balance of the body due in part to the rapid change in circulating blood volume. When the fluid removal rate is more rapid than the plasma refilling rate of the body, intravascular blood volume decreases. The resulting imbalance has been linked to complications such as hypotension, loss of consciousness, headaches, vomiting, dizziness and cramps experienced by the patient, both during and after dialysis treatments. Continuous quantitative measurement of parameters relating to the circulating blood volume (in real-time) during hemodialysis reduces the chance of dialysis-induced hypotension, and otherwise optimizes dialysis therapy regimes by controlling fluid balance and aiding in achieving the appropriate dry weight for the patient.

Pressure sensors can be incorporated in dialyzers used for hemodialysis to achieve continuous monitoring of fluid balance of the body. During dialysis, obtaining fluid input and output pressures experienced at various inlets and outlets of dialyzers is easier than obtaining flow rates at these inlets and outlets. Flow rates, on the other hand, are better parameters to be used in determining the effectiveness of a dialyzer during hemodialysis. Using embodiments of the disclosure, pressure measurements may be applied to determine fluid flow rates in a dialyzer. This is beneficial because blood flow rates are especially difficult to model due to the variability of blood structure. Embodiments of the disclosure further employ and develop adaptive models that utilize measured pressures and flow rates of particular dialyzers to determine relationships between flow rates and dialyzer fluid pressures. Embodiments of the disclosure thus provide for using pressure measurements to determine and monitor the effectiveness of a hemodialysis process.

Modeling flow rates out of a dialyzer during hemodialysis is important since blood can coagulate and become more viscous, making expected flow rates differ from actual flow rates. In hemodialysis, interpreting pressure readings may be difficult, but matching fluid flow rates to a hemodialysis pump flow rate is comparatively easier. In some embodiments, pumps are set to flow at a particular flow rate, so if an estimated fluid flow rate is different from the pump flow rate, then a patient undergoing hemodialysis or a caregiver of the patient is alerted to a problem. Potential problems during hemodialysis may include blood coagulation, kinks in fluid tubing, leakage in fluid tubing, air bubbles in tubing, etc. Thus, when variance between expected and commanded flow rates exceeds a threshold, this may be an indication of a problem. For example, air bubbles in dialysate flowing through a tubing to the dialyzer impacts pressure and will result in a lower flow rate.

Flow rate monitoring is an important factor to determining the ultrafiltration rate (UF rate) of extraction of fluids from a patient undergoing dialysis. Currently, determination of UF rate is typically achieved by monitoring and controlling pressures instead of flow rates, such as by: (a) using trans-membrane pressure (TMP); (b) using gravimetric scale measuring the weight of the filtered and collected fluids, or (c) measuring weight of the patient at the end of treatment. The use of TMP in (a) is not very accurate and is susceptible to wide variability in the UF rate. The use of the gravimetric scale in (b) is more accurate, but scales tend to be subjected to turbulence of fluids being pumped. The weight measurement in (c) does not allow for real-time control in an accurate manner.

Flow rate monitoring presents additional technological challenges. When monitoring flow rate during dialysis, flow rate meters have to be attach to tubing properly. If the flow rate meters do not attach properly, then the coupling between the tubing and the meter is not firm and an accurate measurement will not be made. This is especially difficult since patients may move during the dialysis process, rendering the tubing subject to movement and testing the attachment of the flow rate meters to the tubing. In addition to patient movement, the flow rate meters or flow rate sensors may have a 20% error (e.g., an ultrasonic sensor) and 5% error at best (e.g., an inflow sensor). In addition to the error tolerance of flow rate sensors, tubing properties changes during dialysis and coupling errors may result from such changes. For example, at the beginning of a dialysis treatment, tubing is usually more rigid but becomes more compliant towards the end of the treatment due to the compressions of the peristaltic pump strokes on the tubing.

In addition to the technological challenges that flow rate monitoring presents, financial challenges are also an impediment. Since ultrasonic sensors are not very accurate, inflow sensors would be desirable. Tubing used in dialysis is disposable, as are many medical supplies that sustain extended exposure to fluids from a patient. Thus, if inflow sensors are used in tubing, the inflow sensors would be exposed to the fluids from the dialysis patient. As such, the inflow sensors would have to be disposed, thus increasing the cost of disposables needed for the hemodialysis process.

Pressure measurements on the other hand are easier to obtain externally, thus providing non-invasive measurements. Additionally, compared to flow rate meters, pressure sensors are much more accurate. Utilizing some embodiments of the disclosure, there are no disposable costs associated with developing a model for the dialyzer. In some embodiments, multiple dialyzers can be modeled and a barcode system may be implemented. A scan of a barcode on a disposable tubing and a scan of a barcode for the dialyzer may be used to extract properties of the disposable tubing and properties of the dialyzer to determine an applicable dialyzer model. When using pressure measurements, pressure sensors may be placed as close as possible to dialysate in, dialysate out, blood in, and blood out ports of the dialyzer.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients, e.g., on a Monday-Wednesday-Friday schedule or a Tuesday-Thursday-Saturday schedule. While the invention is not limited to a particular number of hemodialysis systems located at a clinic, or a specific type of hemodialysis system, the general operation of the hemodialysis system 12 is helpful for understanding an exemplary environment in which embodiments of the invention may be utilized.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed blood is returned from the dialyzer through extracorporeal tubing 24 and return needle or catheter 26. In some parts of the world, the extracorporeal blood flow may receive a heparin drip to prevent clotting although that is not shown in FIG. 1. The excess fluids and toxins are removed by clean dialysate liquid which is supplied to the dialyzer 22 via tube 28 and removed for disposal via tube 30. A typical hemodialysis treatment session takes about 3 to 5 hours in the United States.

In some embodiments, the optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes light-emitting diode (LED) photo emitters that emit light at substantially 810 nm, which is isobestic for red blood cell hemoglobin, at substantially 1300 nm, which is isobestic for water, and at substantially 660 nm, which is sensitive for oxygenated hemoglobin. The blood chamber 32 includes lenses so that the sensor emitters and detectors can view the blood flowing through the blood chamber 32, and determine the patient's real-time hematocrit value and oxygen saturation value using ratiometric techniques generally known in the prior art.

For purposes of background, when a typical patient 10 arrives at a hemodialysis clinic, the patient is first checked in and then weighed on a scale at the clinic. The patient then is seated in an assigned hemodialysis chair where a clinician inserts an arterial and venous needle into the patient's access. The access may be an artificial shunt or a natural fistula that has been surgically tied from an artery to a vein. Alternatively, as mentioned previously, the connection might be through a catheter. Next, the dialysis lines 18, 24 are prefilled with normal saline and connected to the patient. The peristaltic pump 20 is started slowly and the normal saline is flushed through the lines 18, 24 as well as the dialyzer 22 into the patient 10, as arterial blood is pulled into the dialysis circuit. The normal saline tends to lubricate or prime the system for blood passage. Also, since saline is less dense than blood, any leaks in the system will be immediately apparent before starting the hemodialysis process. In the exemplary environment of FIG. 1, the peristaltic pump 20 is shown as a blood pump, and a dialysate pump is not shown. A dialysate pump may be provided in hemodialysis system 12 in addition to the blood pump. Examples of systems with both a dialysate pump and a peristaltic pump are described, for example, in U.S. Pat. Nos. 8,597,505 and 8,137,553 which are both incorporated by reference in their entireties. In other implementations, a dialysate pump is not necessary and dialysate flows through tubing 30 using gravity.

Figure 2:
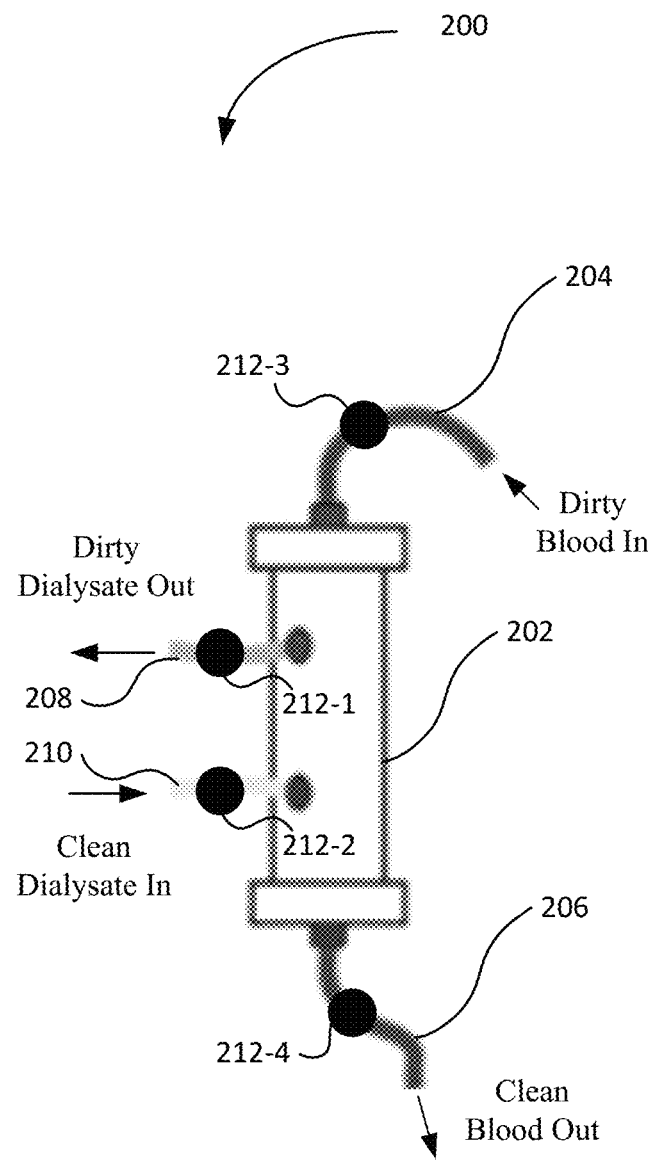
FIG. 2 illustrates fluid flow in a dialyzer according to an embodiment of the disclosure.

FIG. 2 illustrates fluid flow for a dialyzer 202 according to an embodiment of the disclosure. Dialyzer 202 may be used in the environment provided in FIG. 1. Dialyzer 202 is connected to an arterial blood line 204, a venous blood line 206, a dialysate in line 210, and a dialysate out line 208. In FIG. 2, provided in the fluid flow diagram are pressure sensors that measure fluidic pressures close to the line ports of the dialyzer 202. The pressure sensors may include, for example, a dialysate out pressure sensor 212-1, a dialysate in pressure sensor 212-2, a blood in (arterial) pressure sensor 212-3, and a blood out (venous) pressure sensor 212-4. Blood flows into the dialyzer 202 through the arterial blood line 204 and flows out of the dialyzer 202 through the venous blood line 206. Dialysate flows into the dialyzer 202 through the dialysate in line 210 and flows out of the dialyzer 202 through the dialysate out line 208. In dialysis, fluidic pressures and flow rates across a dialyzer are important factors to maintain a successful dialysis treatment, where the pressure inside the dialyzer membrane is higher than the pressure outside the dialyzer membrane, in order for ultra-filtration to occur and therefore forcing fluid to transition from the blood to the dialysate.

Embodiments of the disclosure utilize measurements of pressures across the dialyzer inlets (204 and 210) and outlets (206 and 208) to detect, for example, line leakages and line occlusions. The pressures that may be measured from dialyzer 202 include: the input pressure of arterial blood line, the output pressure of the venous blood line, the input pressure of the dialysate in line, and the output pressure of the dialysate out line. U.S. Pat. Nos. 8,597,505 and 8,137,553 provide schematic diagrams of hemodialysis systems showing similar locations for placing pressure sensors to measure pressure at these identified lines of a dialyzer.

Figure 3:
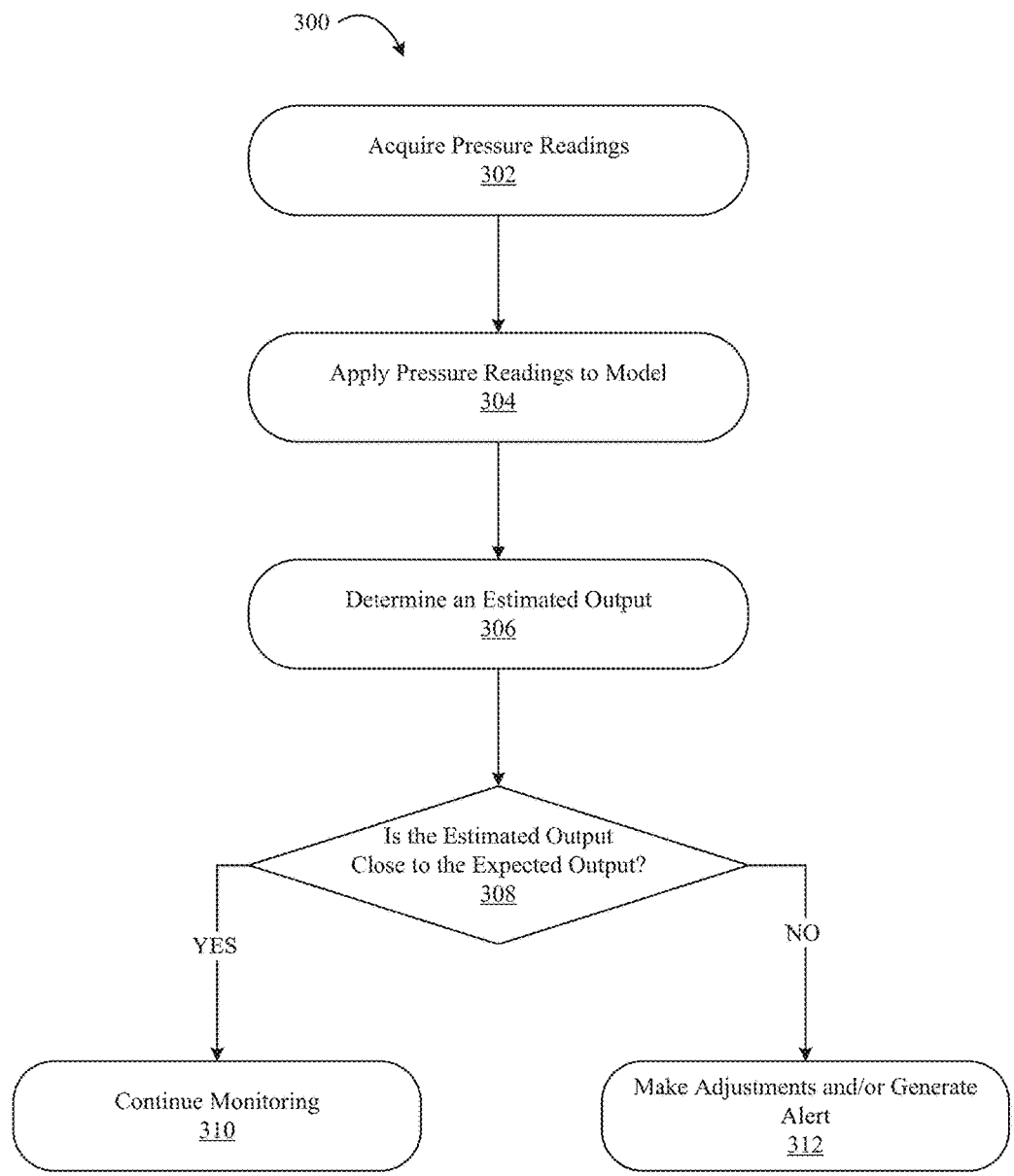
FIG. 3 is a flow diagram illustrating a process for using pressure readings to make estimates of parameters related to a dialyzer.

FIG. 3 provides an overview of a process of using pressure measurements or pressure readings to monitor a hemodialysis process. At step 302, the hemodialysis system 12 acquires pressure readings from pressure sensors 212-1, 212-2, 212-3, and/or 212-4. The hemodialysis system 12 includes electronic components such as one or more processors and one or more non-transitory computer readable media to store and utilize the pressure readings in computations and other types of analysis. The hemodialysis system 12 may also include Universal Serial Bus (USB) connections that interface with the pressure sensors 212 to receive analog pressure readings from the pressure sensors 212. Examples of such systems are described in U.S. Pat. No. 8,597,505.

At step 304, the hemodialysis system 12 applies the pressure readings to one or more models. The one or more models may include one or more adaptive models obtained through machine learning algorithms Properties and relationships between the various pressures across the dialyzer inlets and outlets are modeled in order to adaptively arrive at characteristic models describing the dynamic relationship between the input pressure(s) and outputs pressure(s) or pump flow rate(s) or equivalently pump rotations per minute.

The one or more adaptive models may be developed based on an initial offline training and measurement setup. For example, an adaptive model developed may be dialyzer specific, given the dialyzer's dimensional and flow path characteristics. Thus, a model can be developed for each type of dialyzer and saved in the memory of the hemodialysis system 12 for selection upon identification of the disposable and/or dialyzer type or model. A model is first created to define the relationship between measured pressures and corresponding flow rates; then, after the model has been trained, the model can be used in real-time to estimate flow rates from real-time measured pressures using the model coefficients.

In an exemplary embodiment, the one or more models can be developed in a two-step process including a first offline step and a second real-time step. By estimating dynamic flow rates based on measured pressure rather than estimating flow rates from pump rates (e.g., per motor RPM), exemplary embodiments of the disclosure are able to achieve a relatively more accurate evaluation. This also helps detect variation in increased flow path resistance such as formation of clotting or leaks or effect of air bubbles on treatment UF rate.

In the first step, the one or more models can be developed using adaptive methods that enable either a single input single output (SISO) type model structure, or a single input multiple outputs (SIMO) structure, or more preferably a multiple inputs and single output (MISO) type model structure, or even more preferably a multiple input multiple output (MIMO) type model structure to help create relationships between one or more input measured pressures and one or more flow rates as output, or alternatively one or more input measured pressures and one or more other pressures as output.

The first step of model development occurs offline where a dialyzer is set up similar to FIG. 1, and flow meters or flow sensors are incorporated in the tubing paths for tubing 18, 24, 28, and 30. When developing a model offline, a patient is not connected to the hemodialysis system 12. Pressure measurements at the dialyzer 22 are then recorded for various commanded pump flow rates from the peristaltic pump 20 and dialysate pump if applicable. If using gravity, then the gravitational effect for dialysate fluid flow through the dialyzer is taken into account. The outputs of the various flow meters or flow sensors incorporated in the tubing are then measured. Once enough data points are measured, then the adaptive model for the dialyzer 22 is developed using these measured values. Note that since this offline measurement using flow meters or flow sensors is only performed without a patient and during training of the model, the flow meters or flow sensors used do not contribute to added disposable costs of hemodialysis treatments Inline flow meters may be used to improve accuracy of flow rate measured during this process.

The second step of model development occurs in real-time while the models developed in the first step are applied during treatment (patient connected to hemodialysis system 12). During treatment, real-time measured inputs are used to estimate what the output flow rates or pressures should be, and the differences between estimates and actual measurements are monitored for determining abnormal flow rates or pressures. The real-time application of the model helps alert a user or system on malfunctioning sensors, hardware, or abnormal measurement conditions such as fluid path disposable leaks or occlusions. Additionally, the real-time application of the model allows monitoring and regulating effects of external variables such as temperature on the measurement system, which can help improve the accuracy of the measurement.

In a preferred embodiment, the one or more models are represented using a linear state-space variable model structure which can be used to represent SISO, MISO, SIMO, or MIMO function relationships between input pressures measured at different points in the dialyzer flow path and output flow rates estimated through the dialyzer flow paths. Similarly the linear state-space variable model structure can be used to model relationships between input pressures measured at different points in the dialyzer flow paths and other output pressures measured at other points in the dialyzer flow paths. State-space variables per these model structures capture the forced dynamics of the relationships between the inputs and the outputs of the function represented by multiple order differential equations corresponding to the "state." State-space variables are useful for capturing compliance dynamics when relating input pressure measured at some point in the dialyzer flow path to output flow rates or pressures at some point in the dialyzer flow path. Linear models are useful in relating the linear relationships between a pressure signal measured at some point in the dialyzer flow path to another pressure or flow rate signal at a different point in the dialyzer flow path.

In an exemplary embodiment, a state space system model is described by a state equation and an output equation. The state equation takes the form:

$$x(k+1)=Ax(k)+Bu(k)$$

The output equation takes the form:

$$y(k)=Cx(k)+Du(k)+n(k)$$

where u(k), y(k), and x(k) are time series of real numbers representing the input, output, and state, respectively, of the system; and n(k) is time series of real numbers representing the noise term which is assumed to be independent of the input sequence u(k). k is the discrete time step for the series, and A, B, C, and D indicate the coefficient vectors.

At step 306, the pressure readings applied to one or more models cause an estimated output to be provided by the hemodialysis system 12.

At step 308, the estimated output based on the one or more models is compared against a measured, actual, or expected output. For simplicity and clarity in explanation, the measured, actual, or expected output will be referred to as the expected output. If the estimated output and expected output deviate from one another by a significant margin (e.g., based on determining whether or not the estimated output and expected output are within a predefined range), then adjustments are made to the system and/or an alert or alarm is generated at step 312. What constitutes a significant margin can be characterized as a predefined threshold range relative to the estimated output or the expected output, which may, for example, be a function of the estimated output or the expected output (e.g., a predefined range defined in terms of an amount or percentage greater than and/or less than the estimated output or the expected output). If the estimated output and the expected output are within a tolerance (i.e., does not differ by a significant margin), then at step 310 the hemodialysis system 12 continues monitoring the output by performing steps 302 through steps 308 during the hemodialysis process.

Figure 4:
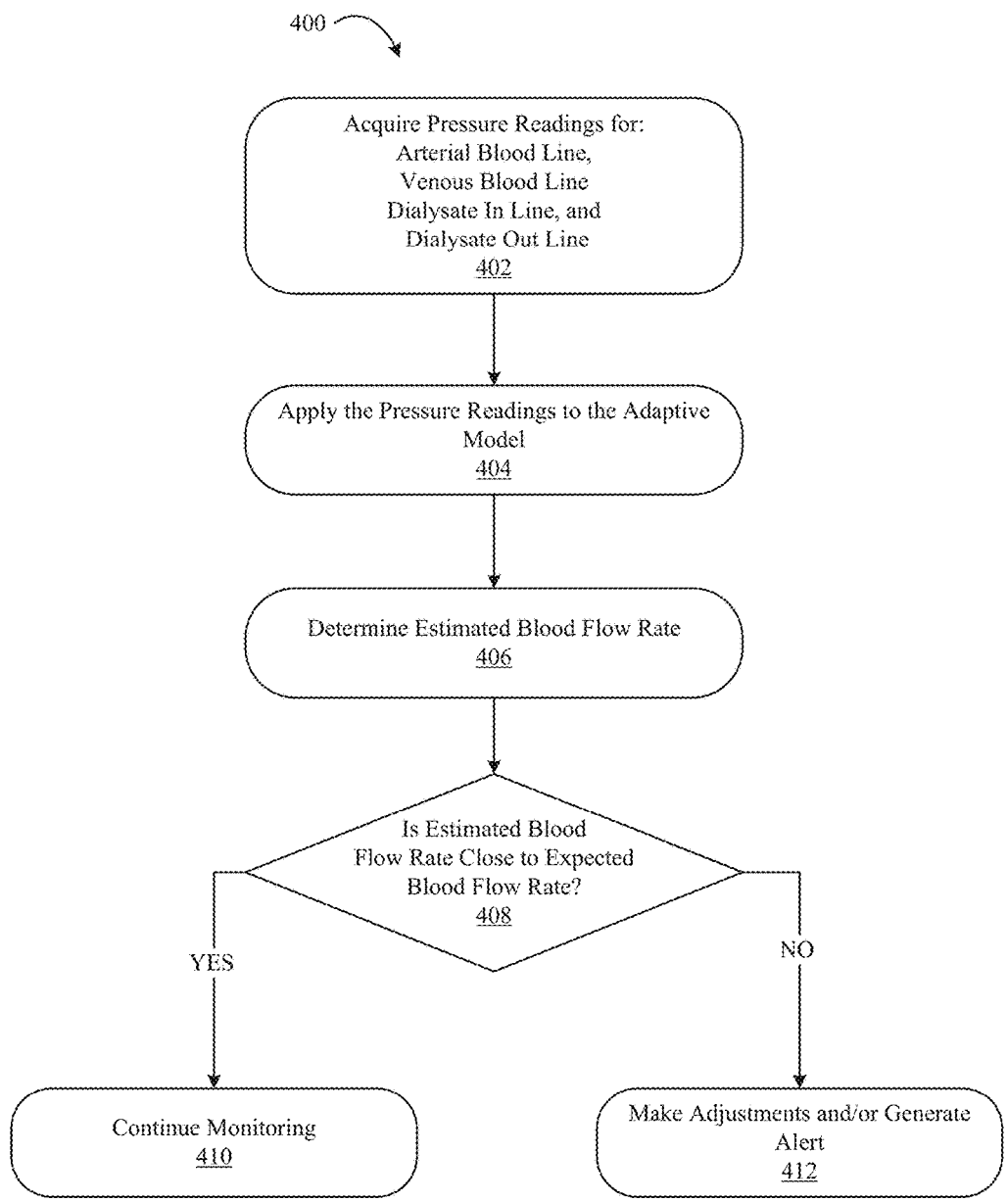
FIG. 4 is a flow diagram illustrating a process for estimating blood flow rate according to an embodiment of the disclosure.
Figure 5:
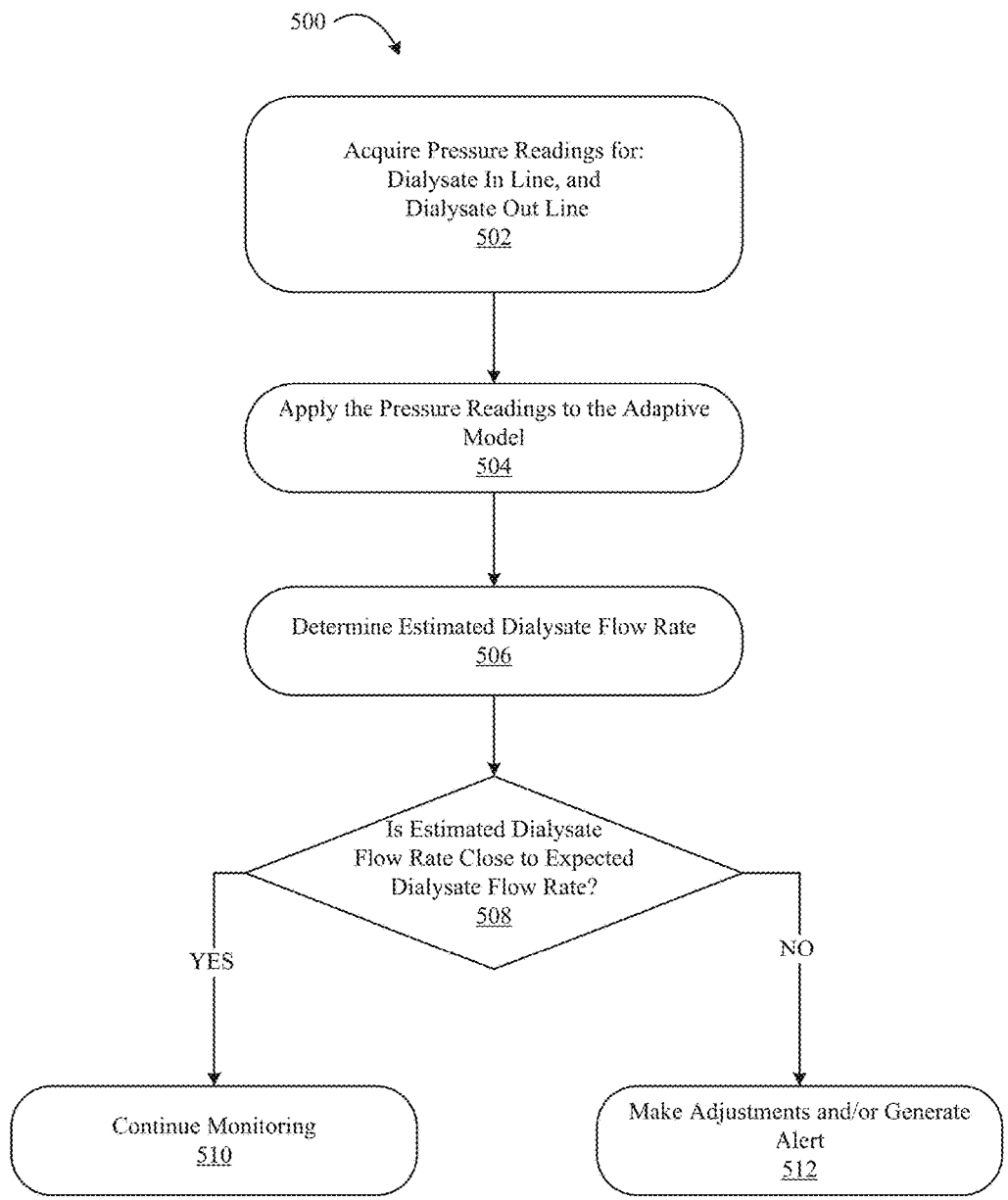
FIG. 5 is a flow diagram illustrating a process for estimating dialysate flow rate according to an embodiment of the disclosure.
Figure 6:
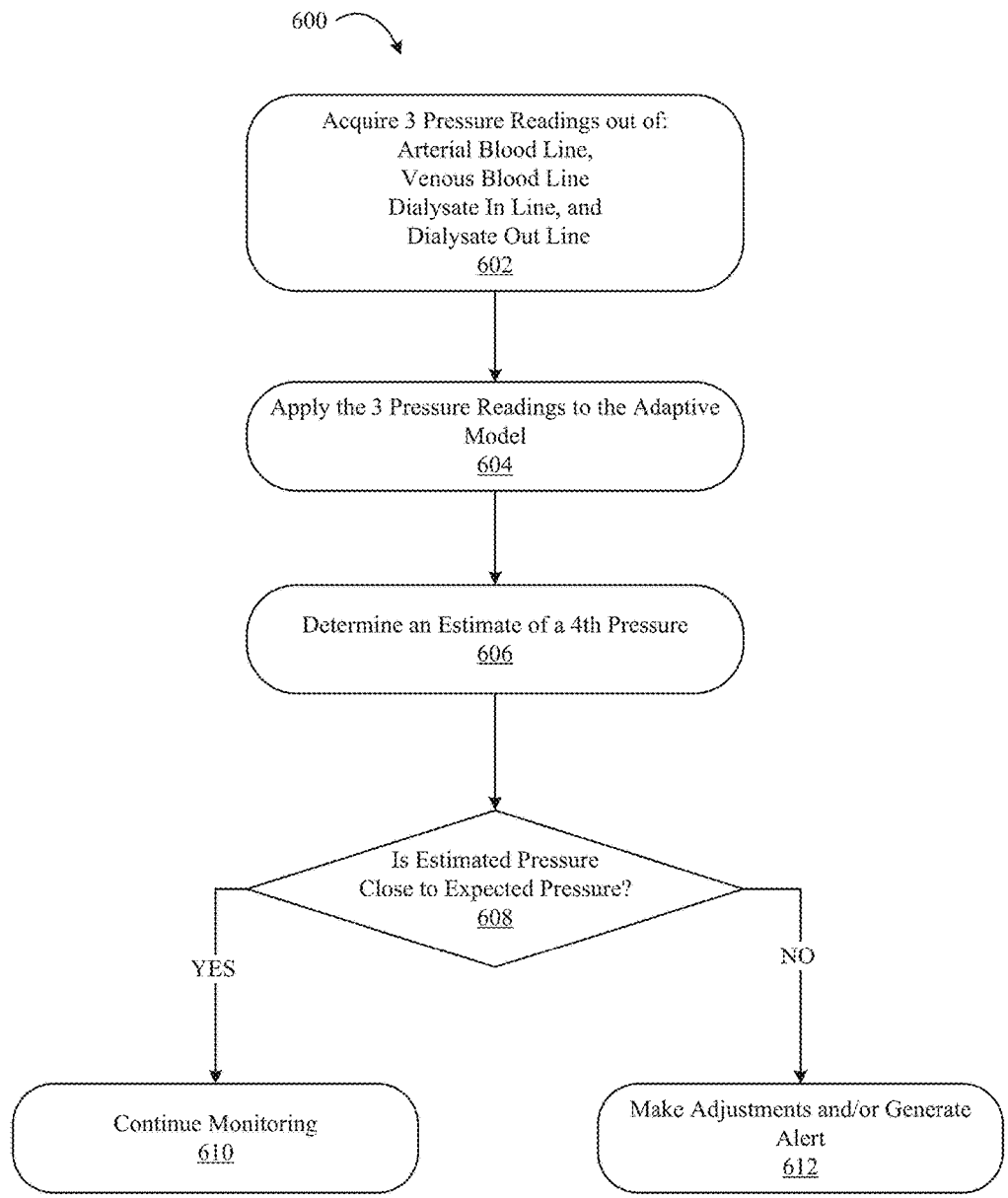
FIG. 6 is a flow diagram illustrating a process for estimating pressure according to an embodiment of the disclosure.

FIGS. 4-6 provide exemplary implementations and variants of the general process depicted in FIG. 3. FIG. 4 is a flow diagram illustrating a process for estimating blood flow rate according to an embodiment of the disclosure. At step 402, the hemodialysis system 12 acquires pressure readings for the arterial blood line 204, the venous blood line 206, the dialysate in line 210, and the dialysate out line 208 from pressure sensors 212-3, 212-4, 212-2, and 212-1, respectively. Example pressure sensors that may be used include flow through pressure sensors, for example, Transpac disposable pressure transducer by ICU Medical, Inc., and non-invasive pressure sensors, for example, load cells by FUTEK Advanced Sensor Technology.

At step 404, the hemodialysis system 12 applies the pressure readings to one or more adaptive models.

At step 406, the hemodialysis system 12 determines estimated blood flow rate using the outputs of the one or more adaptive model. This step is important because even when the peristaltic pump 20 is set to a specific blood flow rate, that flow rate may not be realized due to environmental factors, such as line occlusions or leakages. The pressure readings determined at step 402 will reflect actual conditions at the dialyzer 22, and when these readings are used with the model, the estimated blood flow rate obtained is a more accurate flow rate compared to the commanded flow rate for the peristaltic pump 20.

At step 408, the hemodialysis system 12 determines whether the estimated blood flow rate is close to what is expected (i.e., the expected blood flow rate). In some embodiments, the expected blood flow rate is estimated from actual rotations per minute (RPM) of the peristaltic pump 20. An RPM encoder feedback is used to determine an estimate for the expected blood flow rate for comparison to the estimated blood flow rate using the adaptive model from step 406.

In another embodiment, the estimated blood flow rate obtained at step 406 is converted to blood volume to determine efficacy of the ultrafiltration process. Thus, an expected blood volume based on an elapsed time may be determined to better control the ultrafiltration process.

When the estimated blood flow rate is not close to the expected, then at step 412 adjustments are made in the hemodialysis process and/or an alert or alarm is generated. For example, tubing for the arterial blood line or venous blood line may be occluded or leaky thereby causing the discrepancy between the estimated blood flow rate and the expected blood flow rate. By finding this discrepancy, these problems may be fixed by compensation or regulation of the flow rate by automatic closed loop adjustment of pump flow rates, or an alarm can be generated. The pump flow rates may be increased or decreased automatically to more closely align with the desired target flow rates. Tuning system performance to meet a desired target blood or dialysate flow rates facilitates a clinical outcome of dialysis to the patient or a dialysis therapy objective, such as ultrafiltration rate or total volume, arterial or venous pressure, or patient's electrolyte conductivity balance, or patient's urea clearance, and so on.

For example, when an estimated pressure is determined to be either high or low in comparison to an expected target pressure level, then a high pressure may be interpreted by the hemodialysis system 12 as a line occlusion or tube kinking issue causing the high pressure, or a low pressure can be interpreted by the hemodialysis system 12 as an indication of a presence of compressible air in the line or a line leakage leading to reduced pressure. In response to such events the hemodialysis system 12 can decrease the flow rate to lower a detected high pressure, or increase the flow rate to increase the pressure so that target pressure levels are maintained.

Similarly, blood flow rates during dialysis treatment may increase or decrease due to arterial line access conditions, patient movements resulting in needle dislodgement, tubing line kinking, blood clotting, needle infiltration, or arterial line occlusion under negative pressure. Such conditions may require an adjustment to the dialysate flow rate to be increased or decreased in order to maintain a target dialyzer's trans-membrane pressure (TMP) differential between its blood path and dialysate path. Regulating the TMP facilitates maintaining target clinical clearance levels for electrolyte concentration or clearance. Electrolytes may include magnesium (Mg), calcium (Ca), sodium (Na), potassium (K), phosphorous (P), and chloride (Cl). Regulating the TMP also facilitates maintaining target concentration and clearance for compounds of interest during dialysis, for example, bicarbonate, glucose, creatinine, or blood urea. Regulating the TMP may also be used to maintain a target conductivity measurement. Utilizing embodiments of the disclosure to model and estimate flow rate from pressure provides better control or regulation of the target clinical electrolyte concentration or clearance, urea clearance, and conductivity levels.

In another example, blood leaks through the dialyzer fibers or blood clots in the dialyzer can be detected when comparing the estimated blood pump flow rate and the actual pump flow rate. Blood clots can occur in the dialyzer due to air exposure in the dialyzer header, due to lack of Heparin in the blood, or due to low blood flow rates.

Another exemplary adjustment includes dynamic recalibration when one or more models are deemed inadequate. That is, when there are no signs of blood clots, line occlusions or leakages, or any other discernable hardware malfunction, then the one or more adaptive models can be adjusted to minimize the discrepancy between the estimated blood pump flow rate and the actual pump flow rate.

The alarms that are generated for a user may include, for example, an alarm or alert indicating that blood or dialysate flow rate is too low, or flow rate is too high, or pressure is too low, pressure is too high, or that one of the foregoing problems are detected (e.g., line occlusion, tube kinking, presence of air, line leakage, needle dislodgement, blood clotting, needle infiltration, etc.). An alert or alarm message may be generated on a local machine (such as a host device), and/or to a remote monitoring center, to prevent further clinical risk to the patient such as a delay in treatment, discontinuation of treatment, or inefficient dialysis. The alarm may include, for example, an auditory alert generated at the host device or the remote monitoring center, a visual alert such as a message or graphic displayed at the host device or the remote monitoring center, or other forms of auditory, visual, data logging, and/or haptic notifications.

FIG. 5 is a flow diagram illustrating a process for estimating dialysate flow rate according to an embodiment of the disclosure. At step 502, the hemodialysis system 12 acquires pressure readings for the dialysate in line 210 and the dialysate out line 208 from pressure sensors 212-2 and 212-1, respectively.

At step 504 the pressure readings obtained at step 502 are applied to an adaptive model.

At step 506, the hemodialysis system 12 determines an estimate for the dialysate flow rate. At step 508, if the estimated dialysate flow rate is close to what is expected (i.e., the expected dialysate flow rate according to a dialysate pump), then the hemodialysis system 12 continues monitoring at step 510, else, adjustments are made and/or an alert or alarm is generated at step 512. For example, air bubbles present in the dialysate can affect the pressures realized at the dialysate inlets and outlets, and therefore, directly affect the actual flow rates realized as estimated by the system model. In one embodiment, at step 512, a compensation or regulation of the flow rate can be applied to achieve a more accurate target flow rate, and therefore, a more accurate UF rate to meet the target desired UF rate. Also, the blood flow rate can be increased or decreased to meet a target arterial or venous pressure. Similarly, the blood flow rate and/or dialysate flow rate can be increased or decreased to meet a target electrolyte concentration or conductivity, target concentration or clearance of bicarbonate, glucose, creatinine, or blood urea. In another embodiment, an alarm can be indicated to the user for removal of air bubbles from the dialysate line. In another embodiment, the system can trigger an alarm in response to a line leak or a line occlusion that is detected to alert the user at the presence of a problem that can result in a failure to meet a target UF rate or volume.

The dialysate pump used to estimate the actual dialysate flow rate may be a variable flow pump or a constant flow pump. As in FIG. 4, the process in FIG. 5 may be used to determine line occlusions, leakages, and kinks in the dialysate tubing. FIG. 5 shows that two pressures as inputs may be used to determine a flow rate, that is, dialysate in line pressure and dialysate out line pressure may be used with an adaptive model to determine dialysate flow rate. In another embodiment, a similar method may be employed to estimate blood flow rate given arterial blood line 204 pressure and venous blood line 206 pressure.

FIG. 6 is a flow diagram illustrating a process for estimating pressure according to an embodiment of the disclosure. At step 602, the hemodialysis system 12 acquires from pressure sensors 212 three pressure readings out of the four fluid lines, that is, the arterial blood line 204, the venous blood line 206, the dialysate in line 210, and the dialysate out line 208. For example, the three pressure readings may be pressure readings from the arterial blood line 204 pressure sensor 212-3, the venous blood line 206 pressure sensor 212-4, and the dialysate in line 210 pressure sensor 212-2.

At step 604, the hemodialysis system 12 applies the three pressure readings to an adaptive model.

At step 606, the hemodialysis system 12 determines an estimate of a fourth pressure from the adaptive model using the three pressure readings. For example, if the three pressure readings were the arterial blood line 204, the venous blood line 206, the dialysate in line 210, then the hemodialysis system 12 determines an estimate for the pressure of the dialysate out line 208 using the model and the three pressure readings.

At step 608, the estimated pressure is compared to actual pressure readings from pressure sensor 212 to determine whether the estimated pressure is close to what is expected (i.e., the expected pressure). A discrepancy may exist between the estimated pressure and the actual pressure when there is a line leakage, line occlusion, or blood clots. As in the previous embodiments, once the discrepancy is detected, adjustments may be made at step 612, including adjusting the blood flow rate or dialysate flow rate, and/or an alarm may be generated. If no discrepancy exists, then the hemodialysis system 12 continues monitoring the fourth pressure at step 610 utilizing steps 602 through steps 608.

Embodiments of the disclosure provide a method and system for detecting line leaks (in either blood or dialysate lines). Line leaks result in lower than expected flow rates in the blood or dialysate lines. Similarly, embodiments of the disclosure provide a method and system for detecting line occlusions potentially due to tube kinking (in either blood or dialysate lines). Line occlusions result in lower than expected flow rates in the blood or dialysate lines.

Figure 7:
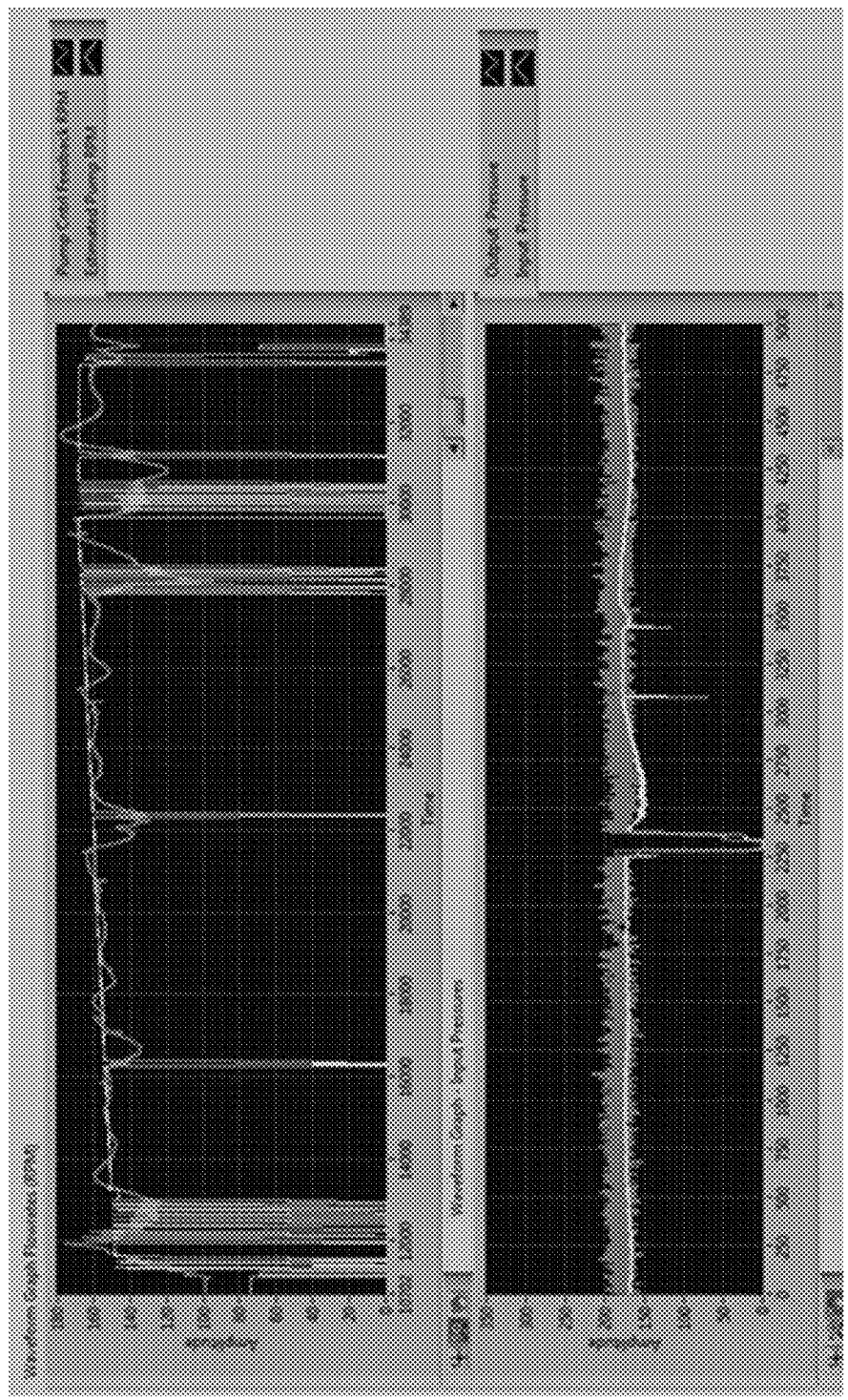
FIG. 7 illustrates blood flow rate estimation using arterial (input) and venous (output) dialyzer pressures according to an embodiment of the disclosure.

FIGS. 7-11 illustrate graphs of different output estimations using measured pressures across a dialyzer according to various embodiments of the disclosure. In FIG. 7, blood flow rate estimation is achieved using arterial and venous dialyzer pressures according to an embodiment of the disclosure. The setup to achieve the results for FIG. 7 is similar to that of the embodiment in FIG. 5. At step 502, pressure readings for arterial blood line 204 and venous blood line 206 are acquired through pressure sensors 212-3 and 212-4, respectively. In FIG. 7, the input pressure and output pressure shown on the bottom are pressure readings for the arterial blood line 204 and venous blood line 206, respectively.

Using these pressures and the procedure provided in FIG. 5, an estimated pump RPM is obtained as shown in FIG. 7. The estimated pump RPM in FIG. 7 is compared to the commanded pump RPM. As shown in FIG. 7, the peristaltic pump 20 can be set at a certain RPM to achieve a certain blood flow rate, but during hemodialysis, real-time blood flow rate can be estimated using the input and output pressures. Real-time blood flow rate shows that the flow rate is not constant or does not behave as smoothly as the commanded pump flow rate.

Figure 8:
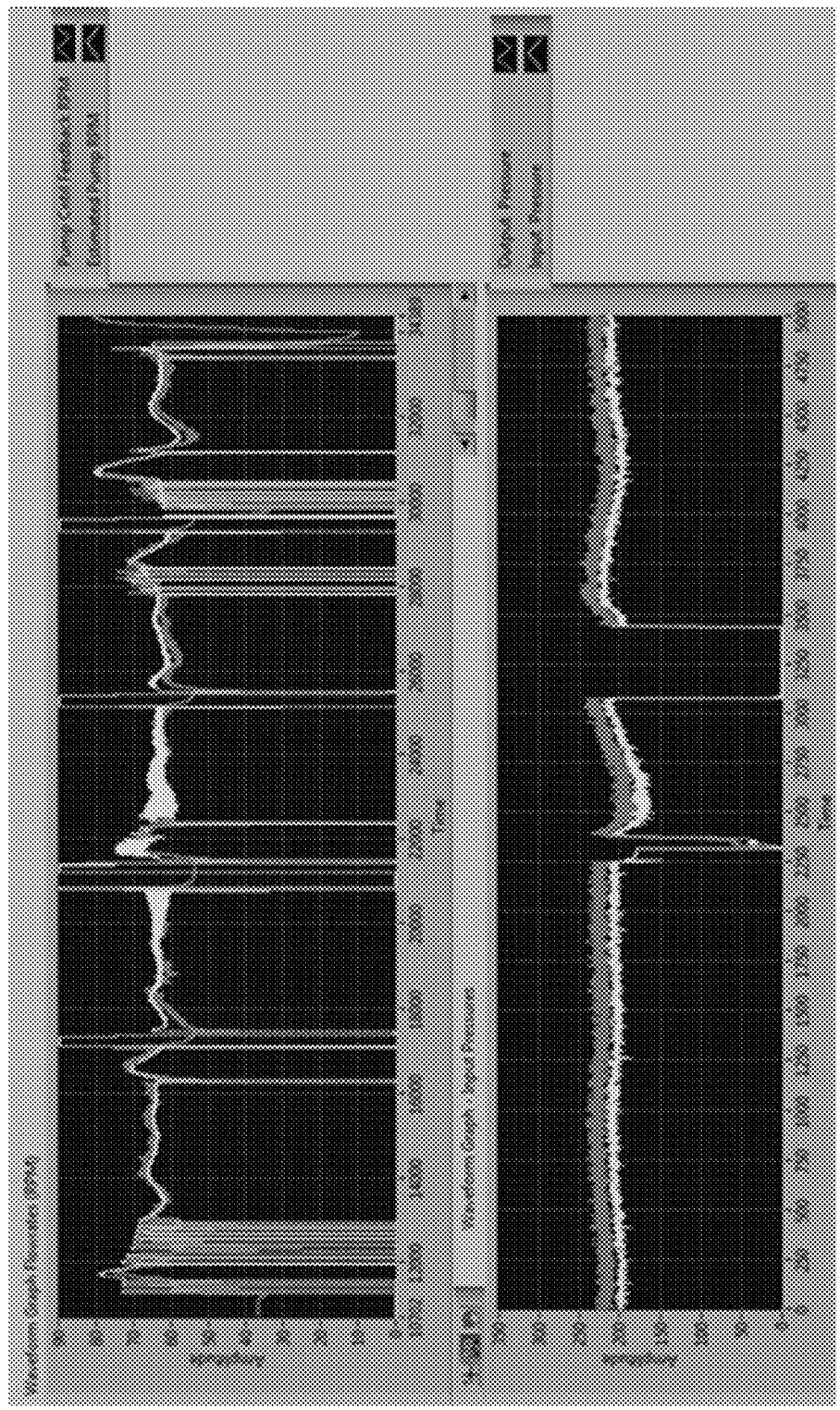
FIG. 8 illustrates dialysate variable pump flow rate estimation using input dialysate and output dialysate dialyzer pressures according to an embodiment of the disclosure.

In FIG. 8, a dialysate variable pump flow rate is estimated using input dialysate and output dialysate dialyzer pressures according to an embodiment of the disclosure. The embodiment of FIG. 5 may be used to realize the dialysate variable pump flow rate estimate of FIG. 8. At step 502, pressure readings for dialysate in line 210 and dialysate out line 208 are obtained by pressure sensors 212-2 and 212-1, respectively. In FIG. 8, the input pressure and output pressure shown on the bottom are pressure readings for the dialysate in line 210 and dialysate out line 208, respectively. Using these pressures and the procedure provided in FIG. 5, an estimated pump RPM is obtained as shown in FIG. 8. The estimated pump RPM in FIG. 8 is compared to a commanded pump RPM. As shown in FIG. 8, when the hemodialysis system 12 incorporates a dialysate pump with a flow rate that may be controlled variably, the estimated pump RPM obtained closely follows the dialysate pump's commanded RPM. The dialysate flow rate may be estimated from the estimated pump RPM.

Figure 9:
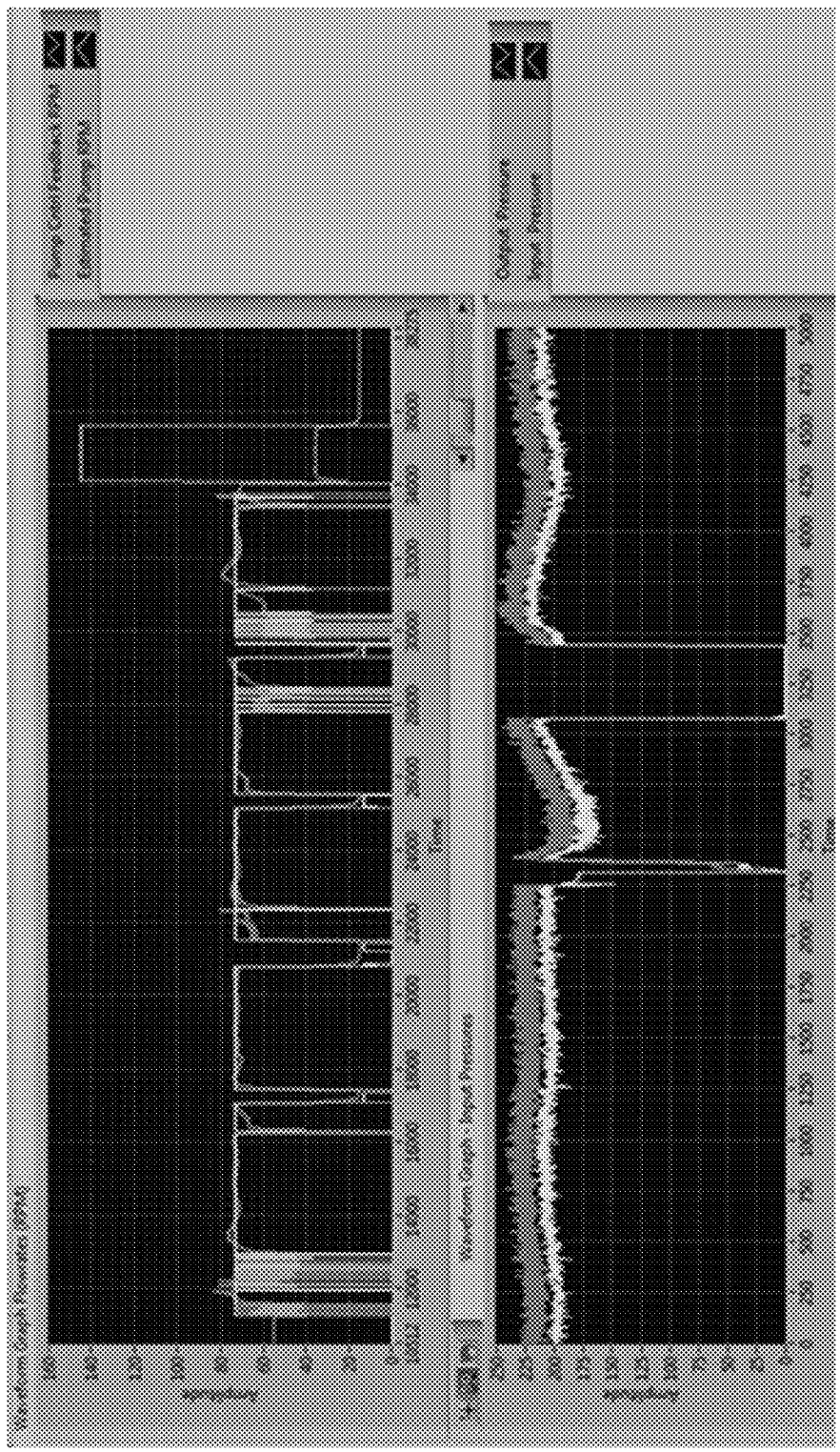
FIG. 9 illustrates dialysate constant pump flow rate estimation using input dialysate and output dialysate dialyzer pressures according to an embodiment of the disclosure.

In FIG. 9, a dialysate constant pump flow rate is estimated using input dialysate and output dialysate dialyzer pressures according to an embodiment of the disclosure. The setup for FIG. 9 is similar to that of FIG. 8, except that the dialysate pump is either ON at a constant RPM or is OFF. The input dialysate and output dialysate dialyzer pressure measurements are provided on the bottom of FIG. 9. FIG. 9 shows that even though the commanded RPM is shown to be zero at certain times, the pressure measurements estimate finite dialysate pump flow rates. As such, even though the dialysate pump may be turned OFF, dialyzer flow rates may be finite and may be determined based on the pressure readings obtained from pressure sensors 212.

Figure 10:
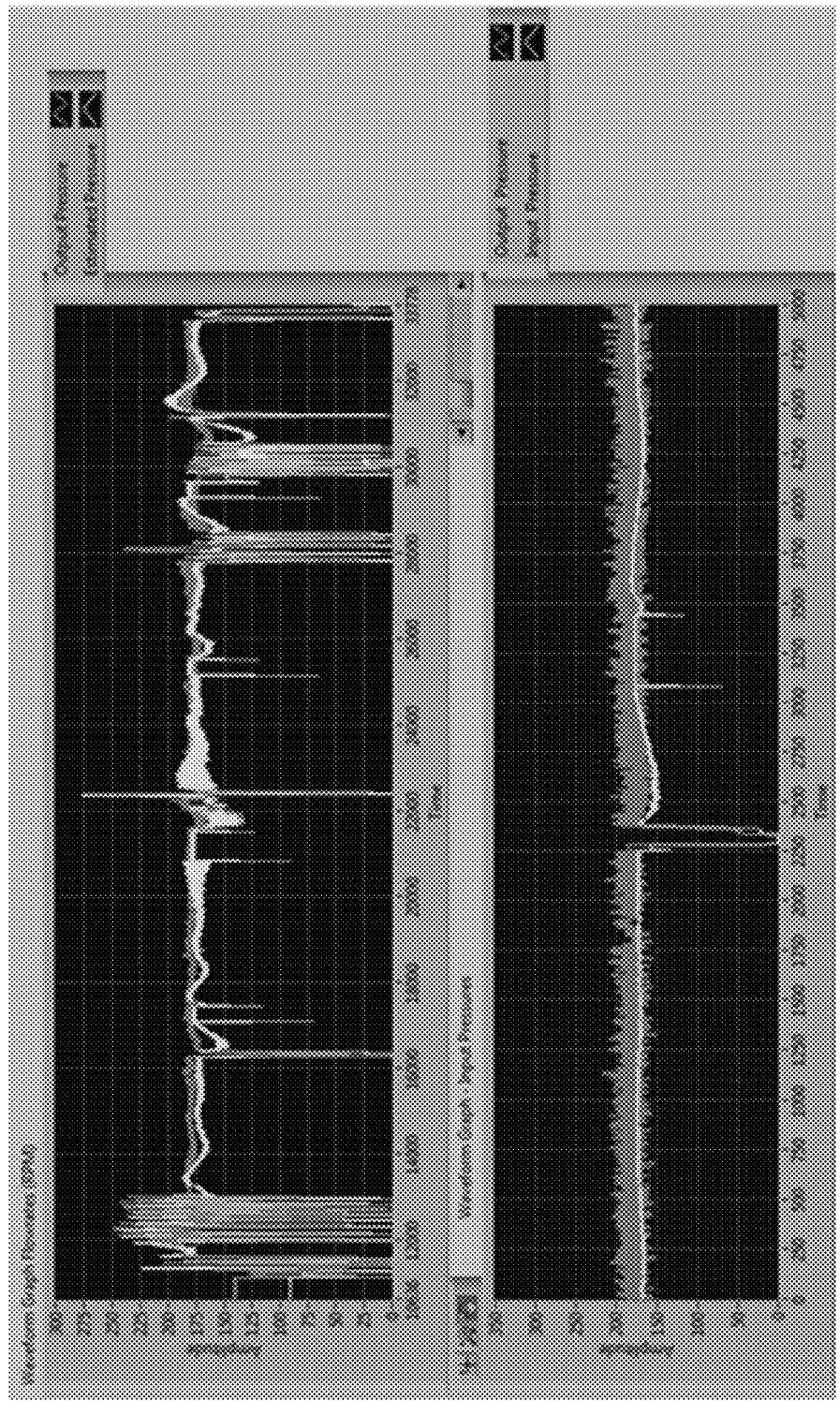
FIG. 10 illustrates venous output pressure estimation using arterial input pressure across the dialyzer according to an embodiment of the disclosure.

In FIG. 10, venous output pressure estimation is accomplished using arterial input pressure across the dialyzer according to an embodiment of the disclosure. FIG. 6 shows a specific embodiment of FIG. 3 where three pressure readings out of the arterial blood line 204 pressure, the venous blood line 206 pressure, the dialysate in line 210 pressure, and the dialysate out line 208 pressure are used to estimate the fourth pressure. The model in FIG. 6 thus receives three pressure inputs and provides one pressure output, signifying that the model used to in FIG. 6 is a MIMO representation of the adaptive dialyzer model. The venous output pressure estimation in FIG. 10 is derived from an embodiment of FIG. 3 that utilizes a SISO representation of the dialyzer model where one pressure input is used by the model to obtain one pressure output. In FIG. 10, the arterial blood line 204 input pressure obtained by pressure sensor 212-3 is used in the SISO model to obtain an estimation of the venous blood line 206 pressure. The SISO model may be obtained in a similar manner already described in the embodiment of FIG. 6. At the bottom of FIG. 10, the arterial input pressure is plotted along with the venous output pressure. At the top of FIG. 10, the venous output pressure obtained by pressure sensor 212-4 is plotted along with the estimated venous output pressure obtained from the SISO model. The two output pressures are shown to have an agreement.

In some embodiments, using a similar setup, a SISO model can be used to determine pressure of the dialysate out line 208 using pressure of the dialysate in line 210. Additionally, the measured or read pressure of the dialysate in line 210 from pressure sensor 212-2 can be used estimate the dialysate in line 210. In general, an output pressure can be estimated with a single input pressure, however, the accuracy of the estimation may be improved when more inputs are used in the model. Therefore, when more information is available as inputs into the adaptive model, the higher the accuracy of the estimation of the output pressure.

Figure 11:
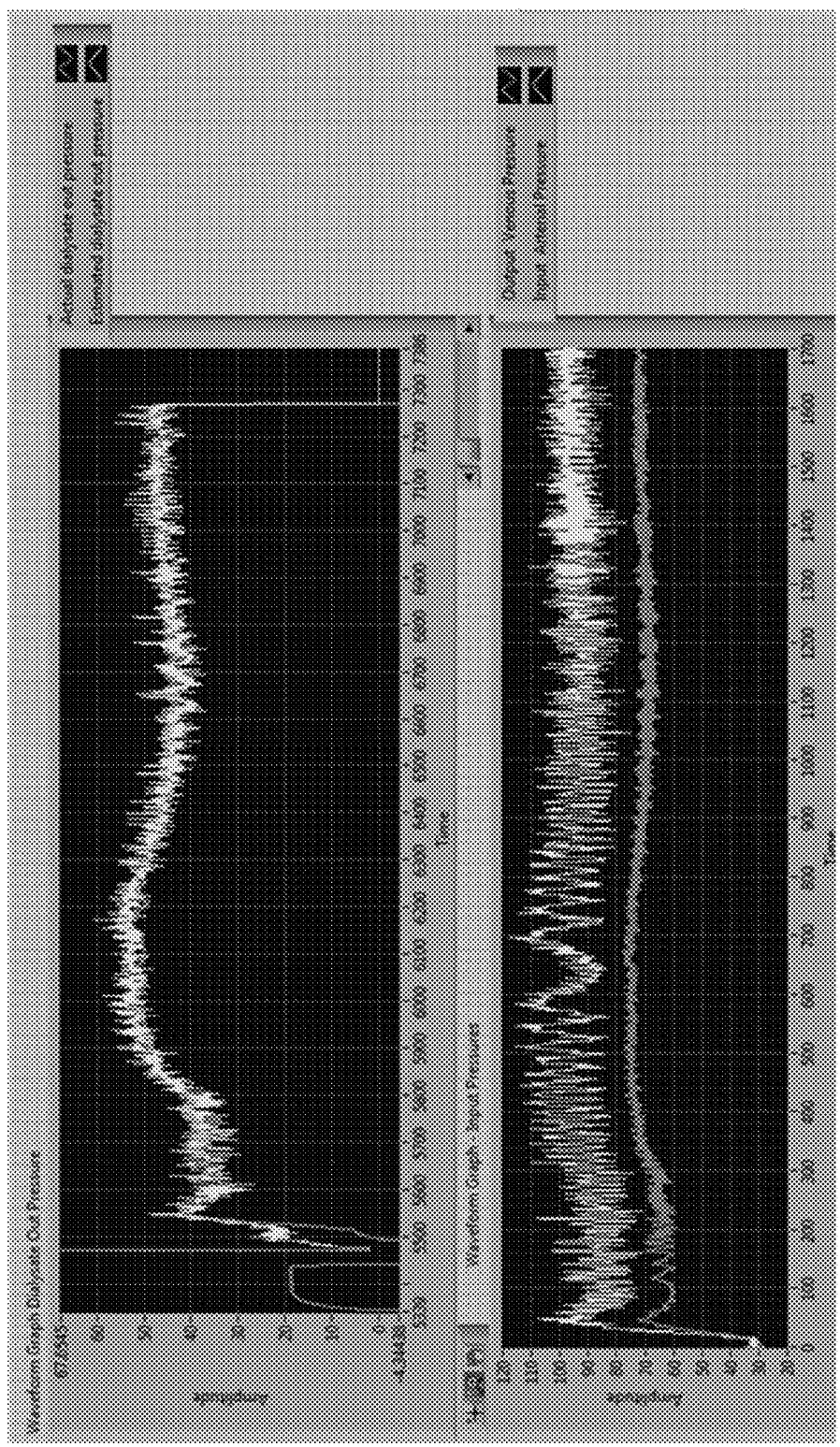
FIG. 11 illustrates dialysate out pressure estimation using arterial pressure and venous pressures according to an embodiment of the disclosure.

In FIG. 11, dialysate out pressure is estimated using as inputs arterial pressure and venous pressures according to an embodiment of the disclosure. Just as FIG. 6 shows an embodiment of FIG. 3 where three pressure readings are used to estimate a fourth pressure, FIG. 11 is obtained using another embodiment of FIG. 3 where two pressure readings are used to estimate a third pressure. Pressure readings for the arterial blood line 204 and the venous blood line 206 are obtained by pressure sensors 212-3 and 212-4, respectively. These pressure readings are applied to a MISO representation of the adaptive dialyzer model to obtain an estimate of the dialysate out line 208 pressure. At the bottom of FIG. 11, pressure readings for the arterial blood line 204 and the venous blood line 206 are plotted. At the top of FIG. 11, dialysate out line 208 pressure reading from pressure sensor 212-1 is compared with estimated pressure of the dialysate out line 208 obtained from the MISO model. The actual pressure reading and the estimated pressure readings are shown to be in agreement.

Figure 12:
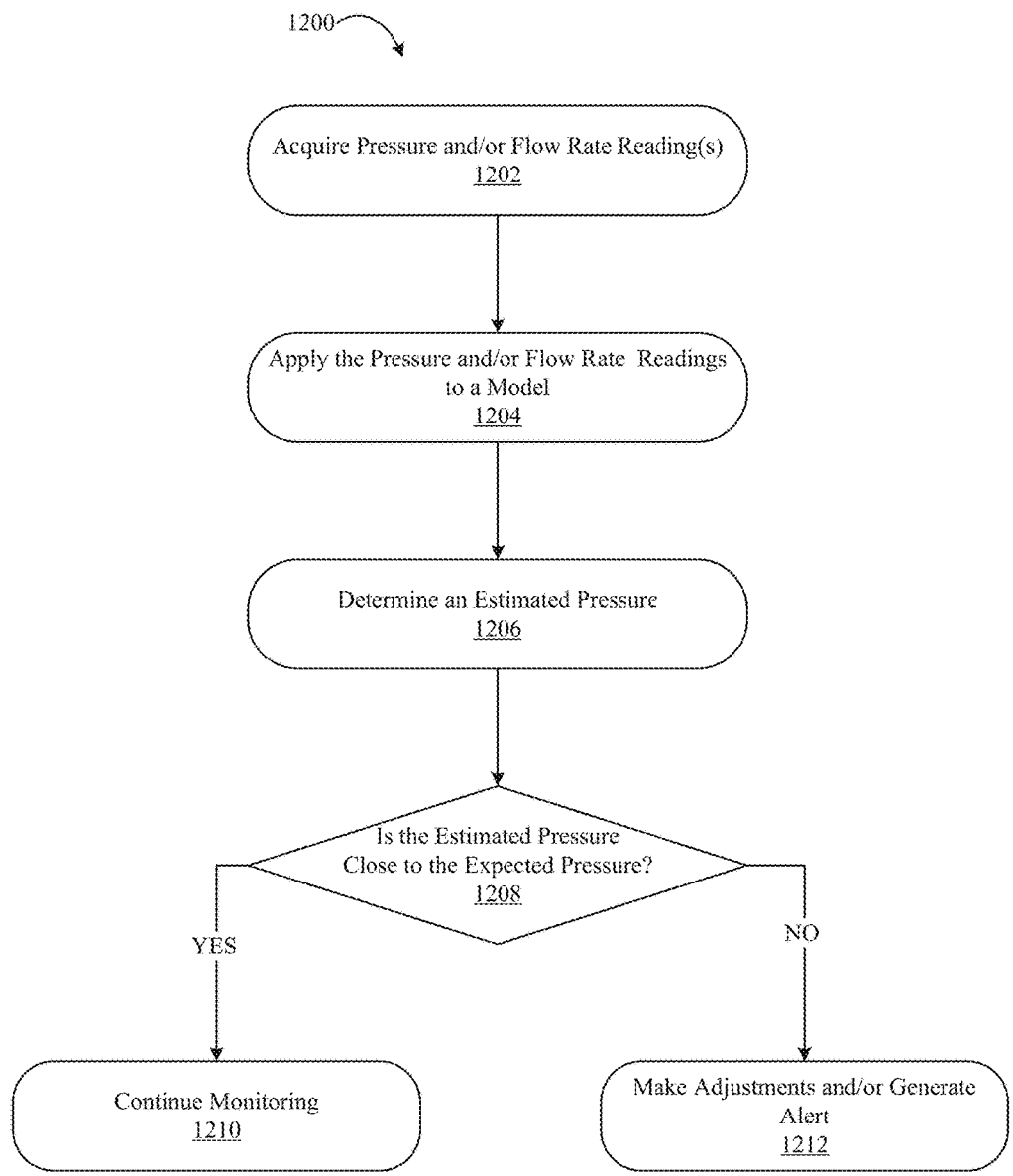
FIG. 12 is a flow diagram illustrating a process for estimating pressure according to an embodiment of the disclosure.

FIG. 12 is a flow diagram illustrating a process for estimating pressure according to an embodiment of the disclosure. At step 1202, the hemodialysis system 12 acquires a flow rate, for example, blood flow rate or dialyzer flow rate, and acquires at least one pressure reading out of the four fluid lines, that is, the arterial blood line 204, the venous blood line 206, the dialysate in line 210, and the dialysate out line 208. As previously discussed flow rates may be acquired from flow meters installed in tubing (if available) or may be determined from pump rates. For example, at step 1202, pump rate of the peristaltic pump 20 may be used to determine a blood flow rate and pressure sensor 212-3 may provide pressure of the arterial blood line 204. In another example, pump rate of the peristaltic pump 20 may be used to determine a blood flow rate and pressure sensor 212-4 may provide pressure of the venous blood line 204. In another example, pump rate of a dialyzer pump may be used to determine a dialysate flow rate and pressure sensor 212-1 may provide pressure of the dialysate out line 208. In another example, pump rate of a dialyzer pump may be used to determine a dialysate flow rate and pressure sensor 212-2 may provide pressure of the dialysate in line 210.

At step 1204, the hemodialysis system 12 applies the flow rate and the pressure sensor reading to an adaptive model.

At step 1206, the hemodialysis system 12 determines an estimate of another pressure from the adaptive model using the flow rate and the pressure reading from step 1202. For example, the hemodialysis system 12 determines pressure of the dialysate out line 208 using dialysate flow rate and pressure of the dialysate in line 210. In another example, the hemodialysis system 12 determines pressure of the dialysate in line 210 using dialysate flow rate and pressure of the dialysate out line 208. In another example, the hemodialysis systems 12 determines pressure reading of the venous blood line 206 using the blood flow rate and the arterial blood line 204. In another example, the hemodialysis system 12 determines pressure reading of the arterial blood line 204 using the blood flow rate and the venous blood line 206.

At step 1208, the estimated pressure is compared to actual pressure readings from pressure sensor 212 to determine whether the estimated pressure is close to what is expected (i.e., the expected pressure). A discrepancy may exist between the two pressures when there is a line leakage, line occlusion, or blood clots. As in the previous embodiments, once the discrepancy is detected, adjustments may be made at step 1212, including adjusting the blood flow rate or dialysate flow rate, and/or an alarm may be generated. If no discrepancy exists, then the hemodialysis system 12 continues monitoring the fourth pressure at step 1210 utilizing steps 1202 through steps 1208.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system for monitoring ultrafiltration rate during hemodialysis using estimated flow rates, the system comprising:
 a dialyzer comprising a first port, a second port, a third port, and a fourth port;
 a plurality of pressure sensors coupled to the dialyzer, the plurality of pressure sensors comprising a first pressure sensor located proximate to the first port, a second pressure sensor located proximate to the second port, a third pressure sensor located proximate to the third port, and a fourth pressure sensor located proximate to the fourth port;
a non-transitory computer readable medium with one or more models stored thereon; and
a processor configured to:
acquire pressure readings from the plurality of pressure sensors,
apply the pressure readings to the one or more models to determine an estimated flow rate,
determine whether the estimated flow rate and an expected flow rate are within a predefined range, and
make adjustments and/or generate an alarm in response to determining that the estimated flow rate and the expected flow rate are not within the predefined range.

2. The system according to claim 1, wherein the adjustments comprise recalibrating the one or more models.

3. The system according to claim 1, wherein the processor is further configured to determine a fluid volume based on the estimated flow rate, and determine whether the fluid volume and an expected fluid volume are within a predefined range.

4. The system according to claim 1, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
the processor is further configured to apply the pressure readings of the four pressure sensors to determine an estimated blood flow rate.

5. The system according to claim 1, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
the processor is further configured to apply the pressure readings of two of the four pressure sensors to determine the estimated flow rate.

6. The system according to claim 5, wherein:
the two of the four pressure sensors are the third pressure sensor and the fourth pressure sensor; and
the estimated flow rate is an estimated dialysate flow rate.

7. The system according to claim 5, wherein:
the two of the four pressure sensors are the first pressure sensor and the second pressure sensor; and
the estimated flow rate is an estimated blood flow rate.

8. The system according to claim 1, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
the processor is further configured to apply the pressure readings of three of the four pressure sensors to determine an estimated fourth pressure.

9. The system according to claim 1, further comprising:
a pump coupled to the dialyzer through a tubing, the pump being configured to establish a medium's flow rate;
wherein the first port is connected to an arterial blood line, the second port is connected to a venous blood line, the third port is connected to a dialysate in line, and the fourth port is connected to a dialysate out line;
wherein the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
wherein the processor is further configured to apply the pressure readings of one of the four pressure sensors and the medium's flow rate to determine an estimated pressure.

10. A method for monitoring ultrafiltration rate during hemodialysis using estimated flow rates, the method performed by an electronic device with a processor and a non-transitory computer readable medium with one or more models stored thereon, the method comprising:
acquiring pressure readings from a plurality of pressure sensors coupled to a dialyzer comprising four ports, wherein the plurality of pressure sensors comprises a first pressure sensor located proximate to a first port of the dialyzer, a second pressure sensor located proximate to a second port of the dialyzer, a third pressure sensor located proximate to a third port of the dialyzer, and a fourth pressure sensor located proximate to a fourth port of the dialyzer;
applying the pressure readings to the one or more models to determine an estimated flow rate;
determining whether the estimated flow rate and an expected flow rate are within a predefined range; and
making adjustments and/or generating an alarm in response to determining that the estimated flow rate and the expected flow rate are not within the predefined range.

11. The method according to claim 10, wherein the adjustments comprise recalibrating the one or more models.

12. The method according to claim 10, further comprising:
determining a fluid volume based on the estimated flow rate, and
determining whether the fluid volume and an expected volume are within a predefined range.

13. The method according to claim 10, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
applying the pressure readings to the one or more models comprises applying the pressure readings of the four pressure sensors to the one or more models to determine an estimated blood flow rate.

14. The method according to claim 10, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
applying the pressure readings to the one or more models comprises applying the pressure readings of two of the four pressure sensors to determine the estimated flow rate.

15. The method according to claim 14, wherein:
the two of the four pressure sensors are the third pressure sensor and the fourth pressure sensor; and
the estimated flow rate is an estimated dialysate flow rate.

16. The method according to claim 14, wherein:
the two of the four pressure sensors are the first pressure sensor and the second pressure sensor; and
the estimated flow rate is an estimated blood flow rate.

17. The method according to claim 10, wherein:
the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line; and
applying the pressure readings to the one or more models comprises applying the pressure readings of three of the four pressure sensors to the one or more models to determine an estimated fourth pressure.

18. The method according to claim 10, wherein:
wherein the first port is connected to an arterial blood line, the second port is connected to a venous blood line, the third port is connected to a dialysate in line, and the fourth port is connected to a dialysate out line;
the first pressure sensor measures pressure at the arterial blood line, the second pressure sensor measures pressure at the venous blood line, the third pressure sensor measures pressure at the dialysate in line, and the fourth pressure sensor measures pressure at the dialysate out line;
wherein a pump is coupled to the dialyzer through a tubing, the pump being configured to establish a medium's flow rate; and
applying the pressure readings to the one or more models comprises applying the pressure reading of one of the four pressure sensors and the medium's flow rate to the one or more models to determine an estimated pressure.

19. A non-transitory computer readable medium for monitoring ultrafiltration rate during hemodialysis using estimated flow rates, the non-transitory computer readable medium having processor-executable instructions stored thereon, the processor-executable instructions, when executed, facilitating performance of the following:
acquiring pressure readings from a plurality of pressure sensors coupled to a dialyzer,
wherein the dialyzer comprises a first port connected to an arterial blood line, a second port connected to a venous blood line, a third port connected to a dialysate in line, and a fourth port connected to a dialysate out line, and
wherein the plurality of pressure sensors comprises a first pressure sensor located proximate to the first port for measuring pressure at an arterial blood line, a second pressure sensor located proximate to the second port for measuring pressure at a venous blood line, a third pressure sensor located proximate to the third port for measuring pressure at a dialysate in line, and a fourth pressure sensor located proximate to the fourth port for measuring pressure at a dialysate out line;
applying the pressure readings to one or more models to determine an estimated flow rate;
determining whether the estimated flow rate and an expected flow rate are within a predefined range; and
making adjustments and/or generating an alarm in response to determining that the estimated flow rate and the expected flow rate are not within the predefined range.

20. The non-transitory computer readable medium according to claim 19, wherein the adjustments comprise recalibrating the one or more models.

* * * * *